(12) United States Patent
Thibodeau et al.

(10) Patent No.: US 8,710,212 B2
(45) Date of Patent: Apr. 29, 2014

(54) STARCH NETWORKS AS ABSORBENT OR SUPERABSORBENT MATERIALS AND THEIR PREPARATION BY EXTRUSION

(75) Inventors: Claude Thibodeau, Lachine (CA); David Bergeron, La Prairie (CA); Isabelle Bolduc, Chambly (CA); Claude Couture, Westmount (CA); Nicolas Nourry, Longueuil (CA)

(73) Assignee: Archer Daniels Midland Company, Decatur, IL (US)

( * ) Notice: Subject to any disclaimer, the term of this patent is extended or adjusted under 35 U.S.C. 154(b) by 1081 days.

(21) Appl. No.: 10/550,748

(22) PCT Filed: Mar. 26, 2004

(86) PCT No.: PCT/CA2004/000473
§ 371 (c)(1),
(2), (4) Date: Nov. 9, 2006

(87) PCT Pub. No.: WO2004/085481
PCT Pub. Date: Oct. 7, 2004

(65) Prior Publication Data
US 2007/0179291 A1 Aug. 2, 2007

(30) Foreign Application Priority Data
Mar. 26, 2003 (CA) .................................... 2423712

(51) Int. Cl.
*C08B 31/00* (2006.01)
*A61L 15/28* (2006.01)
*A61L 15/60* (2006.01)

(52) U.S. Cl.
CPC ................. *A61L 15/28* (2013.01); *A61L 15/60* (2013.01); *C08B 31/003* (2013.01)
USPC ........................................................ 536/47

(58) Field of Classification Search
CPC ........ A61L 15/28; A61L 15/60; C08B 31/003
USPC ........................................................ 536/47
See application file for complete search history.

(56) References Cited

U.S. PATENT DOCUMENTS

| | | | |
|---|---|---|---|
| 3,345,358 A | 10/1967 | Inklaar | 536/106 |
| 3,951,947 A | 4/1976 | Schanefelt et al. | 536/106 |
| 4,098,997 A | 7/1978 | Tessler | 536/106 |
| 4,117,222 A | 9/1978 | Holst et al. | 536/50 |
| 4,219,646 A | 8/1980 | Rubens | 536/109 |
| 4,369,308 A | 1/1983 | Trubiano | 536/106 |
| 4,452,978 A | 6/1984 | Eastman | 536/111 |
| 4,454,055 A | 6/1984 | Richman et al. | 252/194 |
| 4,973,447 A | 11/1990 | Seib et al. | 426/549 |
| 5,079,354 A | 1/1992 | Gross et al. | 536/111 |
| 5,187,272 A | 2/1993 | Katcher et al. | 536/102 |
| 5,221,733 A | 6/1993 | Koskan et al. | 530/333 |
| 5,342,932 A | 8/1994 | Katcher et al. | 536/102 |
| 5,367,068 A | 11/1994 | Lane et al. | 536/124 |
| 5,470,968 A | 11/1995 | Katcher et al. | 536/102 |
| 5,612,384 A | 3/1997 | Ross et al. | 521/64 |
| 5,720,822 A | 2/1998 | Jeffcoat et al. | 127/65 |
| 5,997,945 A * | 12/1999 | Shasha et al. | 427/213.3 |
| 6,001,408 A | 12/1999 | Dudacek et al. | 426/516 |
| 6,010,574 A | 1/2000 | Jeffcoat et al. | 127/65 |
| 6,218,532 B1 | 4/2001 | Mark et al. | 536/124 |
| 6,261,376 B1 | 7/2001 | Jeffcoat et al. | 127/65 |
| 6,358,580 B1 | 3/2002 | Mang et al. | 428/35.7 |
| 6,413,567 B1 | 7/2002 | Dudacek et al. | 426/578 |
| 6,488,980 B1 | 12/2002 | Jeffcoat et al. | 426/661 |
| 6,541,060 B2 | 4/2003 | Jeffcoat et al. | 426/578 |
| 2001/0007665 A1 | 7/2001 | Illum et al. | 424/400 |
| 2002/0037352 A1 | 3/2002 | Messager et al. | 426/549 |
| 2002/0090446 A1 | 7/2002 | Jeffcoat et al. | 426/661 |
| 2003/0008049 A1 | 1/2003 | Wilson et al. | 426/549 |
| 2003/0027901 A1 | 2/2003 | Richardson et al. | 524/47 |
| 2003/0143277 A1 | 7/2003 | Ameye et al. | 424/487 |
| 2003/0180430 A1 | 9/2003 | Fryirs | 426/589 |

FOREIGN PATENT DOCUMENTS

| | | |
|---|---|---|
| CA | 2308537 | 11/2000 |
| CA | 2362006 | 5/2002 |
| CA | 2426478 | 10/2003 |
| EP | 0000247 | 8/1982 |
| EP | 0799837 | 10/1997 |
| EP | 0900807 | 3/1999 |
| EP | 1176255 | 1/2002 |
| EP | 0769501 | 6/2002 |
| GB | 1554002 | 10/1979 |
| GB | 1576475 | 10/1980 |
| GB | 2043668 | 10/1980 |
| NL | 9100249 | 9/1992 |

(Continued)

OTHER PUBLICATIONS

Sigma-Aldrich, "Particle Size Conversion Table"; also available online at http://www.sigmaaldrich.com/chemistry/stockroom-reagents/learning-center/technical-library/particle-size-conversion.html; last accessed Nov. 4, 2010.*
Tester, R. F. et al., Cereal Chemistry, "Swelling and Gelatinzation of Cereal Starches. I. Effects of Amylopectin, Amylose, and Lipids", 1990, vol. 67, No. 6, pp. 551-557.*
Anderson RA. Water Absorption and Solubility and Amylograph Characteristics of Roll-Cooked Small Grain Products. Cereal Chem 59:265-269, 1982.*
Buchholz and Graham, "Modern superabsorbant polymer technology," Wiley-VCH, New York, 147:239-241, 1998.
Chang et al., "Preparation of starch phosphates by extrusion," *J. Food Sci.*, 57:203-205, 1992.
Edana, "Determination of fluid retention capacity in saline after centrifugation," Method 441.2-02, EDANA, Brussels, 2002.
Edana, "Free-swell capacity by gravimetric determination," Method 440.2-02, EDANA, Brussels, 2002.

(Continued)

*Primary Examiner* — Brandon Fetterolf
*Assistant Examiner* — Yih-Horng Shiao
(74) *Attorney, Agent, or Firm* — Vincent Kung; Mark Roberts

(57) ABSTRACT

The present invention relates an absorbent material consisting of a molecular network of starch molecules, the starch molecules comprising an amylopectin content of at least 90% (w/w). The molecular network can either be comprised of self-entangled starches or cross-linked starches.

9 Claims, 5 Drawing Sheets

(56) References Cited

FOREIGN PATENT DOCUMENTS

| WO | WO 97/00620 | 1/1997 |
| --- | --- | --- |
| WO | WO 98/35992 | 8/1998 |
| WO | WO 99/31167 | 6/1999 |
| WO | WO 99/64508 | 12/1999 |
| WO | WO 00/05973 | 2/2000 |
| WO | WO 00/21581 | 4/2000 |
| WO | WO 00/35504 | 6/2000 |
| WO | WO 01/19404 | 3/2001 |
| WO | WO 02/088188 | 11/2002 |

OTHER PUBLICATIONS

Hirsch and Kokini, "Understanding the mechanism of cross-linking agents through swelling behavior and pasting properties of cross-linked waxy maize starches," *Cereal Chem.*, 79:102-107, 2002.

Kim et al., "Effects of phosphorylating salts and temperature on the preparation of rice starch phosphates by extusion," *Stach/Starke*, 8-9:280-286, 1999.

Kulicke et al., "Swelling and rheological studies of some starch hydrogels," *Starch/Starke*, 41:140-146, 1989.

Nabeshima et al., "Functional properties of pregelatinized and cross linked cassava starch obtained by extrusion with sodium trimetaphosphate," *Carbohydr. Polym.*, 45:347-353, 2001.

Narkrugsa et al., *Starch/Starke*, 44:81-90, 1992 (Abstract).

Riccardo, "Water-absorbant polymers: A patent survey," *J. Macromol Sci. Rev. Macromol Chem. Phys.*, 34:607-662, 1994.

Salay et al., "Production and properties of starch phosphates produced by the extrusion process," *Starch/Starke*, 42:15-17, 1990.

Whistler et al., "Starch: Chemistry and Technology," Academic Press, Orlando, pp. 287, 1984.

Xanthos, "Reactive extrusion: principles and practice," Hanser Publisher, New York, 1992.

\* cited by examiner

STARCH NETWORKS AS ABSORBENT OR SUPERABSORBENT MATERIALS AND THEIR PREPARATION BY EXTRUSION

This application is a national phase application under 35 U.S.C. §371 of International Application No. PCT/CA2004/000473 filed Mar. 26, 2004, which claims priority to Canadian Application No. 2,423,712 filed Mar. 26, 2003. The contents of these applications are incorporated by reference.

FIELD OF THE INVENTION

The present invention relates to starch networks as absorbent or superabsorbent materials as well as to the preparation of these starch networks by extrusion.

BACKGROUND OF THE INVENTION

Superabsorbent polymers are primarily used as absorbents for biological fluids, water and aqueous solutions. Water absorbent materials such as superabsorbent polymers can be employed in various applications, such as in disposable sanitary products (i.e. diapers, incontinence articles, female hygiene products, and absorbent dressings), household articles, sealing materials, humectants (i.e. agricultural products for soil conditioning), anti-condensation coatings, water-storing materials (agriculture/horticulture), absorbent paper products, surgical absorbents, pet litter, bandages, wound dressings and as chemical absorbents. Furthermore, they can also be employed in applications related to the transportation of fresh food or seafood, as well as in food packaging applications.

Polyacrylates, obtained from the polymerization of monomers such as acrylic acids and acrylamides (non-renewable sources), constitute a major portion of the commercially available superabsorbents (Modern Superabsorbent Polymer Technology, Buchholz F. L. and Graham A. T. Eds., Wiley-VCH, New York, 1998). However, their biodegradability is questionable, especially for high molecular weight polymers. Polyacrylates generally contain small amounts of residual monomeric starting materials (i.e. acrylic acids and acrylamides) possessing both toxic and allergenic potential.

Superabsorbent polysaccharide-based grafted-polymers are obtained via the grafting of an unsaturated monomer (acrylonitrile, acrylic acid, acrylamide) onto starch, or, less frequently, cellulose. The so-obtained polymers, also called "Super Slurper", have shown a water absorption ranging from 700 to 5300 g/g in deionised water, and up to 140 g/g in a 0.9% saline solution (Riccardo P. O., Water-Absorbent Polymers: A Patent Survey. J. Macromol. Sci., Rev. Macromol. Chem. Phys., 1994, 607-662 and references cited therein). Despite their very high water absorption capability, the grafted polysaccharides, prepared by radical polymerization, are not known to be biodegradable or hypoallergenic, nor are they prepared from renewable sources.

Polyaspartates have also been described to offer good absorbing properties (Ross et al. U.S. Pat. No. 5,612,384). However, polyaspartates appear to possess several drawbacks regarding their low molecular weight. Moreover, polyaspartates are prepared from non-renewable sources which constitutes an additional drawback (Koskan et al. U.S. Pat. No. 5,221,733). Furthermore, these polymers are strongly ionic and are thus subject to performance fluctuations in saline solutions.

Carboxymethylcellulose (CMC), and carboxymethylstarch (CMS) (Modern Superabsorbent Polymer Technology, Buchholz F. L. and Graham A. T. ed., Wiley-VCH, Toronto, 1998, 239-241; Gross et al. U.S. Pat. No. 5,079,354; Arno et al. U.S. Pat. No. 4,117,222; Thornton et al. PCT WO 00/35504; Mindt et al. GB 1576475; Couture et al. CA 2,362, 006; Annergren et al. PCT WO 00/21581) constitute other known polysaccharide-based superabsorbents. Cost has always been an issue with these superabsorbents, and they can therefore not be used alone in order to compete with the synthetic polymers. Moreover, these polymers are strongly ionic, as is the case for polyacrylates and polyaspartates, rendering them subject to performance fluctuations in saline solutions. Nonetheless, these products can be used in synergistic formulations, leading to cost effective superabsorbent materials (Bergeron CA 2,426,478; Richman et al. U.S. Pat. No. 4,454,055).

Natural polysaccharide-based superabsorbents constitute a very attractive class of polymers, considering that they can be biodegradable and hypoallergenic, in addition to the fact that they are made from renewable sources such as starch. Polysaccharides have been previously used in an extrusion process for the preparation of non-crosslinked starch-based materials as absorbents for liquids (Huppé et al. CA 2,308, 537).

The use of extruders as continuous reactors for processes such as polymerization, polymer modification or compatibilization of polymer blends, involves technologies that are gaining in popularity. These technologies are competing with conventional operations with respect to environmental considerations, efficiency and economic operators. In the case of reactive extrusion, several organic reactions can be conducted in extruders, including polymerization, grafting, copolymer formation, molecular network formation, crosslinking, functionalization and controlled degradation (Reactive Extrusion: Principles and Practice, Xanthos M. Ed., Hanser Publishers, New York, 1992). This technology has been largely applied in the preparation of polysaccharide-based products from renewable sources such as cross-linked starches, and in applications such as food texturing products (Salay E. et al., Starch/Staerke, 1990, 42, 15-17; Nabeshima E. H. et al., Carbohydr. Polym., 2001, 45, 347-353; Narkrugsa W. et al., Starch/Staerke, 1992, 44, 81-90; Chang Y.-H et. al. J. Food Sci., 1992, 57, 203-205; Kim C.-T. et al., Starch/Staerke, 1999, 51, 280-286). However, none of the products cited are absorbent or superabsorbent materials.

Cross-linked starches have been exhaustively studied (Kulicke W. M. et al Starch/Starke, 41, 1989, 140-146; Brine et al. PCT WO 01/19404A1; Ameye et al US App. 2003/0143277; Seib et al. WO 99/64508; Dumoulin et al. PCT WO 98/35992). However, these cross-linked starches (gels) are not absorbent or superabsorbent materials.

Glass-like polysaccharide abrasive grits have been prepared by extrusion processes of native or crosslinked starches (Lane et al. U.S. Pat. No. 5,367,068). An extrusion process for the preparation of a natural gum substitute composed of cross-linked starch, using phosphorous oxychloride, has been disclosed (Hauber et al. PCT WO 97/00620). However, these products are once again not absorbent or superabsorbent materials.

The preparation of absorbent materials consisting of crosslinked starch using trisodium trimetaphosphate in a co-continuous water-oil system has been described (Feil et al. EP 0900807). In order to remove the oil and to recover the starch-phosphate derivative, an organic solvent such as cyclohexane was added, followed by washing with ethanol. The use of oils and organic solvents are important drawbacks of this batch process. They dramatically increase the production cost of this absorbent, while simultaneously complicating the process.

There thus remains a need for new polysaccharide-based absorbent or superabsorbent materials that are non-abrasive, hypoallergenic, and biodegradable, and which can be cost-efficiently produced from renewable natural sources.

The present invention seeks to meet these and other needs.

SUMMARY OF THE INVENTION

The present invention relates to a starch-based absorbent or superabsorbent material, wherein the starch-based material comprises an amylopectin content of at least 90% (weight/weight, referred to hereinafter as w/w). More specifically, the present invention relates to an absorbent or superabsorbent material consisting of a molecular network of starch molecules, the starch molecules comprising at least 90% (w/w) amylopectin. The molecular network of starch molecules can be composed of either self-entangled starch molecules, or cross-linked starch molecules.

The present invention also relates to an absorbent or superabsorbent material comprising a molecular network of starch molecules, wherein the material is preferably a particulate material.

In a first preferred embodiment, the present invention relates to a particulate absorbent or superabsorbent material comprising a molecular network of starch molecules, wherein the material has a centrifuge retention capacity (CRC) of at least 10 g/g and a free swell capacity (FSC) of at least 13 g/g.

Furthermore, the present invention relates to a process for preparing a starch-based absorbent or superabsorbent material, wherein the starch-based material comprises an amylopectin content of at least 90% (weight/weight, referred to hereinafter as w/w). More specifically, the present invention relates to a process for preparing an absorbent or superabsorbent material consisting of a molecular network of starch molecules, the starch molecules comprising at least 90% (w/w) amylopectin. In one particular embodiment, the process involves the steps of mixing a starch comprising at least 90% amylopectin with water to produce a paste; feeding the paste into an extruder to produce an extrudate; aging the extrudate; and grinding the extrudate. In a further particular embodiment, the process involves the steps of mixing a starch comprising at least 90% amylopectin with water, an alkali and a cross-linking agent to produce a paste; feeding the based paste into an extruder to produce an extrudate; aging the extrudate; and grinding the extrudate.

In a second preferred embodiment, the present invention relates to an extrusion process for preparing a particulate absorbent or superabsorbent material comprising a molecular network of starch molecules.

Finally, the present invention relates to an absorbent or superabsorbent mixture comprising a first absorbent or superabsorbent material consisting of a molecular network of starch molecules, the starch molecules comprising at least 90% (w/w) amylopectin, and a second co-absorbent component selected from the group of synthetic polymers, mannose containing polysaccharides, ionic polysaccharides, and natural or synthetic fibers.

Further scope and applicability will become apparent from the detailed description given hereinafter. It should be understood however, that this detailed description, while indication preferred embodiments of the invention, is given by way of illustration only, since various changes and modifications within the spirit and scope of the invention will become apparent to those skilled in the art.

BRIEF DESCRIPTION OF DRAWINGS

Having thus generally described the invention, reference will now be made to the accompanying drawings, showing by way of illustration a preferred embodiment thereof, and wherein.

DETAILED DESCRIPTION OF THE INVENTION

Definitions and Abbreviations (Symbols and Units)

The term "Free Swell Capacity" (FSC), also called absorption, is expressed in grams (g) of substance absorbed (0.9% NaCl solution) per gram (g) of dry sample.

The "term Centrifuge Retention Capacity" (CRC), also called retention, is expressed in grams (g) of substance absorbed (0.9% NaCl solution) per gram (g) of dry sample.

The term "Residence Time" refers to the time taken by the material to get trough the extruder, from the feed port to the die. The residence time is measured by adding a small quantity of material containing a coloring agent into the feed port. The chronometer is started when the colorant enters the barrel and is stopped when coloration is observed at the die exit.

The term "Extrudate Temperature" refers to the temperature of the material at the die exit as measured by a portable thermocouple plunged into one of the die openings.

The term "starch" is understood as being composed of two polysaccharides; amylose and amylopectin. Amylose is a linear polysaccharide having an average molecular weight of about 250,000 g/mol. Amylopectin is a branched polysaccharide (branching via 1,6-α-glucosidic links) having an average molecular weight of about 75,000,000 g/mol ("Starch: Chemistry and Technology", Whistler R. L., Bemiller J. N. and Paschall E. F. Eds., Academic Press, Orlando, 1984, page 287). In plants, amylopectin is stocked in starch granules in a semi-crystalline form. When heated in the presence of water, starch gelatinizes. Its semi-crystalline structure will change to an amorphous, chaotic state.

Figure 1:
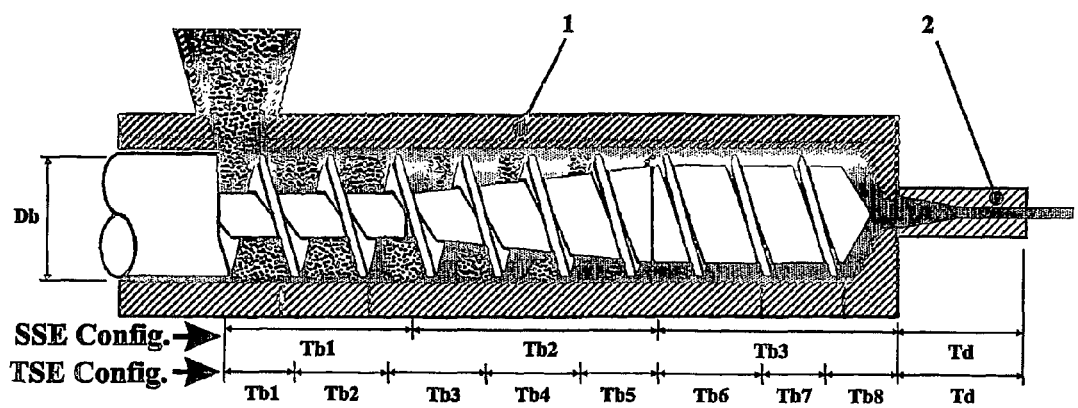
FIG. 1 illustrates a general diagram of an extruder (1) including a die plate (2). In the case of a single screw extruder (SSE), the barrel comprises heating sections (Tb1, Tb2, Tb3, and Td); in the case of a twin screw extruder (TSE), the barrel comprises heating sections (Tb1, Tb2, Tb3, Tb4, Tb5, Tb6, Tb7, Tb8, and Td).
Figure 2:
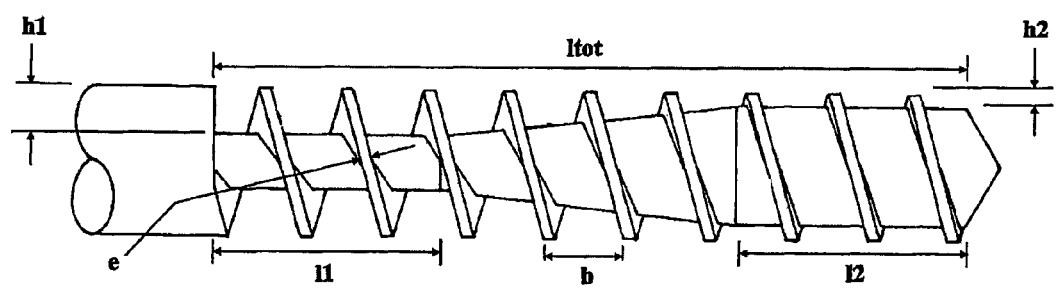
FIG. 2 illustrates various parameters (h1: feeding section flight depth; h2: pumping section flight depth; l1: feeding section length; l2: pumping section length; ltot: total screw length; e: flight width; and b: screw pitch) involved in the screw design of SSEs.
Figure 4:
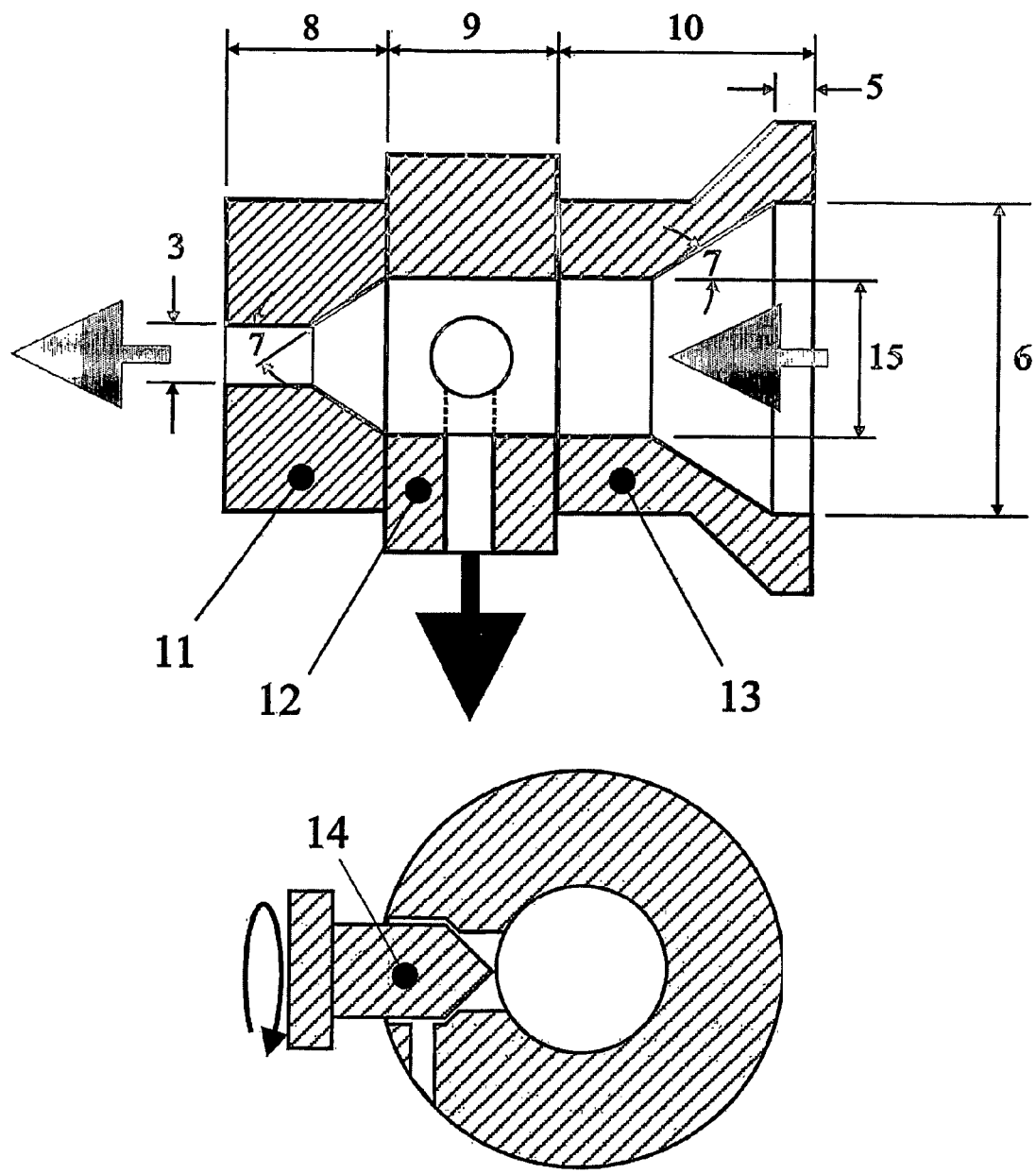
FIG. 4 illustrates an embodiment of the die geometry and valve plate cross-section as used for single screw extruder 2 (SSE2). The die is divided into an opening plate (11), a valve plate (12) and a coupling plate (13) and includes a valve (14) for flow rate adjustments. In this embodiment, the die opening diameter (3) was 8.5 mm; the total die length comprises the length of the opening plate (8) (64 mm), the length of the valve plate (9) (25.4 mm), and the length of the coupling plate (10) (42 mm); the length of the barrel diameter opening (5) was 6.4 mm; the extruder barrel diameter (6) was 44.5 mm; the conical transition angles (7) were both 30°; and the inner diameter (15) of the valve plate (9) was 25.4 mm.

T: Extrudate temperature (° C.); $\Omega$: Screw rotational speed, expressed in RPM (revolutions per minute); Q: Extruder throughput (Kg/h); $Q_{die}$: Die extrusion throughput (Kg/h) (FIG. 4); $Tb_x$: Temperature (° C.) of barrel section X (FIG. 1); Td: Die temperature (° C.) (FIG. 1); HP: Motor power of extruder (Horse Power); $D_b$: Extruder barrel diameter (mm) (FIG. 1); h1: Feeding section flight depth (mm) (FIG. 2); h2: Pumping section flight depth (mm) (FIG. 2); Itot: Total screw length (mm) (FIG. 2); I1: Feeding section length (mm) (FIG. 2); I2: Pumping section length (mm) FIG. 2); b: Screw pitch (mm) (FIG. 2); and e: Flight width (mm) (FIG. 2).

In a broad sense, the present invention relates to a starch-based absorbent or superabsorbent material, wherein the starch-based material is essentially composed of a molecular network of amylopectin molecules consisting of either self-entangled amylopectin molecules, cross-linked amylopectin molecules or a mixture of both self-entangled amylopectin molecules and cross-linked amylopectin molecules.

It was previously illustrated by Huppé et al. (CA 2,308,537) that it is possible to produce a starch-based absorbent having low absorption performances (reported to be 7.5 g/g in 0.9 % NaCl solution) by extrusion. As disclosed hereinafter, it was unexpectedly discovered that the absorption performances of this extruded starch-based material can be significantly improved by increasing the amylopectin content to values in excess of 90% (w/w).

Starch-based absorbent or superabsorbent materials having a CRC of at least 10 g/g and a FSC of at least 13 g/g, are preferred. It was discovered that such starch-based absorbent or superabsorbent materials can be obtained when comprising a molecular network of amylopectin molecules and wherein the amylopectin content is in excess of 90% (w/w). The molecular network of amylopectin molecules should be consisting of either self-entangled amylopectin molecules or cross-linked amylopectin molecules, both of which can be produced using an extrusion process. In cases wherein the extrudate consists of cross-linked amylopectin molecules, the absorbent or superabsorbent material is obtained by cross-linking, aging and grinding the extrudate. Self-entangled starches can be produced by an extrusion process using a specific flow-die configuration, aging and grinding the extrudate. It was discovered that the desired molecular network of amylopectin molecules can be obtained by extruding amylopectin with different cross-linkers, under alkaline conditions. Non-limiting examples of such cross-linkers include sodium trimetaphosphate, sodium tripolyphosphate, phosphorous oxychloride, epichlorohydrin, divinyl sulfone, chlorohydrin, bromohydrin, N,N'-methylenebisacrylamide, alkylenebisacrylamides, ethylene glycol diglycidyl ether, diepoxyalkanes, diglycidyl ethers, glyoxal, glutaraldehyde, dialdehydes, diactivated polyethylene glycols (Couture et al. CA 2,362,006), and mixture thereof.

Examples 1 to 16 (Table 3) illustrate the effect of different extruded amylopectin/amylose blends on the FSC and CRC. The blends were obtained with a single screw extruder using a die (8.5 mm diameter) at about 140° C. These blends produced have an amylopectin content ranging from 72% (levels observed in common corn starch) to 99% (levels observed in pure waxy corn starch). The moisture content of all blends was adjusted to about 30%. The results illustrate that blends having an amylopectin content of at least 90% (w/w) and produced using lower die flow rates (Q) provide for optimal performances.

Typical starches possessing the required amylopectin content (90% w/w) are waxy starches. Waxy starches can be selected from the group consisting of waxy maize starch, waxy wheat starch, waxy rice starch, waxy sorghum starch, waxy potato starch, waxy cassava starch, waxy barley starch and mixtures thereof. A preferred waxy starch is waxy maize starch.

Examples 17 and 18 (Table 4) show two amylopectin extrudates, both produced using an identical extruder throughput "Q", but using a different die extrusion throughput "$Q_{die}$". As illustrated in FIG. 4, the die throughput (flow rate) is valve-controlled. As can be observed from the experimental results, the use of a lower $Q_{die}$ value provides for an extrudate having significantly better FSC and CRC.

The molecular network of cross-linked amylopectin molecules is preferably produced using phosphates cross-linkers since these agents are very well suited to be used in extrusion processes, in addition to being biodegradable. Preferred phosphate cross-linking agents are sodium trimetaphosphate, sodium tripolyphosphate and phosphorous oxychloride. These cross-linkers produce biodegradable phosphate diester linkages. A more preferred phosphate cross-linking agent is sodium trimetaphosphate.

It was discovered that concentrations of cross-linkers ranging from 0.001 to 2.0% (w/w on a dry starch basis without added moisture) provide molecular networks of cross-linked amylopectin molecules having good FSC and CRC performances. In order to achieve efficient cross-linking, the cross-linkers should be mixed with a small amount of alkali. Typical concentrations of alkali range from 0.001 to 2.0% (w/w on a dry starch basis). Typical paste compositions should comprise a water content ranging from 25% to 45% (w/w), an alkali content ranging from 0.001 to 2.0% (w/w on a dry starch basis), a cross-linking agent content ranging from 0.001 to 2.0% (w/w on a dry starch basis), the balance being a starch comprising an amylopectin content of at least 90% (w/w).

Non-limiting examples of alkalis include sodium hydroxide, potassium hydroxide, lithium hydroxide, magnesium hydroxide, calcium hydroxide, beryllium hydroxide, ammonium hydroxide, sodium carbonate, sodium bicarbonate, potassium carbonate, potassium bicarbonate, sodium acetate, potassium acetate, sodium phosphate, sodium hydrogenophosphate, potassium phosphate, potassium hydrogenophosphate and mixture thereof. A preferred alkali is sodium hydroxide.

Examples 19-25 (Table 5) illustrate various amylopectin extrudates produced with different cross-linking agents (also referred too as C-linker) in a twin screw extruder (die diameter of 6 mm) having a moisture content of 30%. As can be observed from the experimental results, the use of cross-linkers results in amylopectin extrudates having significantly better FSC and CRC performances. As can be concluded from the results shown in Table 5, the FSC and CRC performances can be optimized using specific amounts of a given cross-linker and NaOH (Examples 20, 23 and 25).

An efficient extrusion process for the preparation of a starch-based absorbent or superabsorbent material, wherein the starch-based material is essentially composed of a molecular network of amylopectin molecules, either consisting of self-entangled amylopectin molecules or cross-linked amylopectin molecules, is obtained with starch-based starting materials that are in the form of a paste. The paste should be preferably both plastic-like and cohesive. A paste having the required plasticity is obtained when having a moisture content ranging from 25-45% (w/w).

Paste gelatinization using an extruder is a prerequisite to the development of a molecular network of amylopectin molecules, whether consisting of self-entangled amylopectin molecules or cross-linked amylopectin molecules. Gelatinization is a process described as the melting of starch crystallites resulting in a chaotic molecular network upon completion ("Starch: Chemistry and Technology", Whistler R. L., Bemiller J. N. and Paschall E. F. Eds., Academic Press, Orlando, 1984, page 287).

Gelatinization of a starch paste comprising a moisture content ranging from 25-45% (w/w), is preferably carried out using an extrudate temperature of at least 130° C. Such temperatures allow for a fully chaotic molecular network to develop. However, special precautions should be taken in order to avoid any starch degradation. Such degradation leads to extrusion difficulties in addition to providing materials having reduced absorption performances. Starch degradation typically occurs at elevated extrusion temperatures and long residence times in the extruder.

The die extrusion throughput ($Q_{die}$) has a direct impact on the absorption performances (FSC and CRC) of the extruded starch product, irrespective of whether the amylopectin component is self-entangled or cross-linked. For extrudates comprising a self-entangled amylopectin component, the die extrusion throughput is dependent on the particular die geometry used. Indeed, many factors such as die hole diameter, die geometry and die length have a direct impact on the die extrusion throughput. Generally, a lower die extrusion throughput leads to materials having better absorption performances. For extrudates comprising a cross-linked amylopectin component, the die extrusion throughput will once again depend on the particular die geometry used, in addition to being dependent on the cross-linker and alkali levels.

Figure 3:
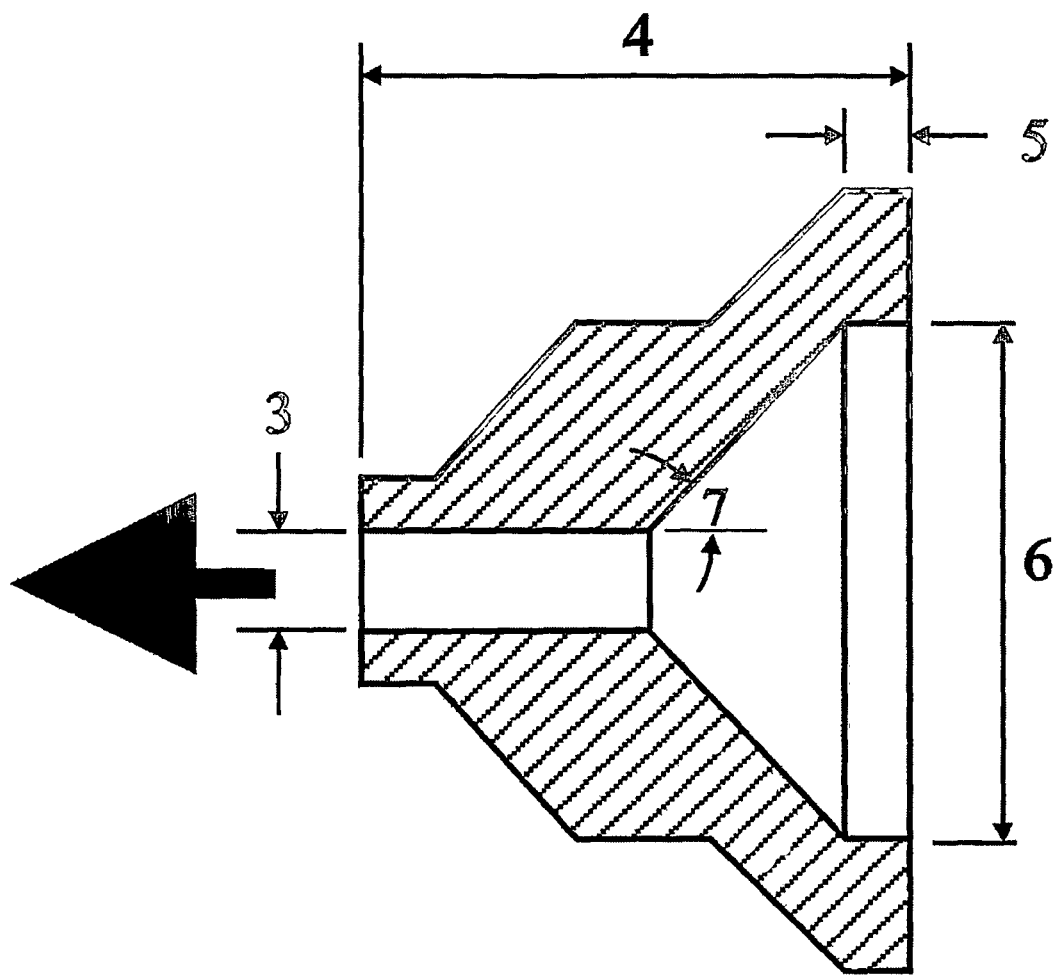
FIG. 3 illustrates an embodiment of the die geometry as used with SSE1 (described in table 1). In this embodiment, the die opening diameter (3) was 8.5 mm; the total die length (4) was 111 mm; the length of the barrel diameter opening (5) was 6.4 mm; the extruder barrel diameter (6) was 44.5 mm; and the conical transition angles (7) were both 30°.

It was unexpectedly discovered that starch-based absorbent or superabsorbent materials comprising a molecular network of amylopectin molecules that are either self-entangled or cross-linked can be efficiently obtained when using a proper combination of die extrusion throughput and die geometry. In a preferred embodiment, the die has the configuration as illustrated in FIGS. 3 and 4. Furthermore, as mentioned herein above, the die extrusion throughput has a direct impact on the absorption performances of the extruded product; lower die flow rates generally leading to extrudates having better absorption performances (FSC and CRC).

A molecular network of amylopectin molecules, whether composed of self-entangled amylopectin molecules or cross-linked amylopectin molecules, can thus be efficiently obtained when considering both the die extrusion throughput and die configuration.

As can be observed from Table 6, an aging process is required in order to fully develop the FSC and CRC performance of the cross-linked amylopectin extrudates. An aging period of 48 hours in a convection oven at 60° C. is generally sufficient. However, special precautions should be taken in order to avoid any starch degradation. Once the aging process completed, the extrudate is ground to provide a particulate absorbent material. Particulate materials are preferred since they can be readily mixed with other absorbent materials.

The FSC and CRC for various particulate materials obtained from self-entangled amylopectin extrudates and cross-linked amylopectin extrudates are shown in Tables 7 and 8 respectively. In a preferred embodiment the particulate material obtained from self-entangled amylopectin extrudates and cross-linked amylopectin extrudates has a particle size ranging from 89 to 589 microns (−30 mesh/+170 mesh). It can be concluded from both Table 7 and 8, that good FSC and CRC characteristics are obtained with particles ranging in size from 89 to 589 microns. The particulate materials shown in Table 7 were obtained with a SSE having an 8.5 mm die diameter, whereas those shown in Table 8 were obtained with a TSE having a 6 mm die diameter.

Starch-based absorbent or superabsorbent materials comprising a molecular network of either self-entangled or cross-linked amylopectin molecules are useful in many applications. These materials are usually mixed with other co-absorbent materials to produce absorbent mixtures or composites. The contribution of the amylopectin component in these mixtures preferably ranges from 1 to 99% (w/w). Non-limiting examples of co-absorbents include, but are not limited to, synthetic superabsorbent polymers, mannose containing polysaccharides, ionic polysaccharides and fibers. The contribution of the co-absorbent(s) in these mixtures preferably ranges from 1 to 99% (w/w).

The synthetic superabsorbent polymers as used herein, are obtained from the radical polymerization or the radical graft polymerization of monomers, non-limiting examples of which include acrylic acid, acrylate salts, acrylic ester, acrylic anhydride, methacrylic acid, methacrylate salts, methacrylic esters, methacrylic anhydride, maleic anhydride, maleic salts, maleate esters, acrylamide, acrylonitrile, vinyl alcohol, vinyl pyrrolidone, vinyl acetate, vinyl guanidine, aspartic acid, aspartic salts and mixture thereof.

Non-limiting examples of mannose containing polysaccharides include guar gum, tara gum, locust bean gum, konjac, mesquite gum, psyllium extracts, fenugreek extracts and mixture thereof.

The ionic polysaccharides that can be mixed with the self-entangled or cross-linked amylopectin absorbent or superabsorbent include both cationic and anionic polysaccharides. In a particular embodiment, the absorbent or superabsorbent amylopectin networks can be mixed with both cationic and anionic polysaccharides. In a preferred embodiment, the absorbent or superabsorbent amylopectin networks are mixed with an anionic polysaccharide. Non-limiting examples of anionic polysaccharides include carboxyalkyl polysaccharides, carboxymethyl cellulose, carboxymethyl starch, oxidized polysaccharides, xanthan, carrageenans, pectin and mixtures thereof.

The fibers can be either natural or synthetic. Non-limiting examples of fibers include cellulose, viscose, rayon, cellulose acetate, Nylon™, polyalkylenes, polyethylene, polypropylene, bi-component fibers, polyesters, polylactides, polypropanediols, Lyocel™, sphagnum and mixture thereof.

The absorbent or superabsorbent materials of the present invention can be employed in a variety of applications such as in disposable sanitary products (i.e. diapers, incontinence articles, feminine hygiene products, and absorbent dressings), household articles, sealing materials, humectants (i.e. agricultural products for soil conditioning), anti-condensation coatings, water-storing materials (agriculture/horticulture), absorbent paper products, surgical absorbents, pet litter, bandages, wound dressings and as chemical absorbents. Furthermore, they can also be employed in applications related to the transportation of fresh food or seafood, as well as in food packaging applications. Moreover, the absorbent or superabsorbent materials of the present invention can be employed to absorb a variety of liquids, non-limiting examples of which include physiological fluids, saline solutions, water and aqueous solutions.

EXPERIMENTAL

Materials

Waxy maize starch having an amylopectin content of at least 99%, and Common corn starch having an amylopectin content of about 72%, were purchased from Cargill Corporation (gel #04230 and 03420 respectively);

Sodium Trimetaphosphate (95-97%), Epichlorohydrin (99%), and N,N'-Methylenebisacrylamide (99%) were purchased from Sigma-Aldrich; and Sodium Hydroxide (99%) was purchased from Laboratoire MAT.

Extruders

Two different extruders, a single screw extruder (SSE) and a co-rotating intermeshing twin screw extruder (TSE) were used (Tables 1 and 2). The Screw design for both the SSE and TSE configuration is illustrated below in Table 2.

TABLE 1

Single and Twin screw extruders.

Figure 6:
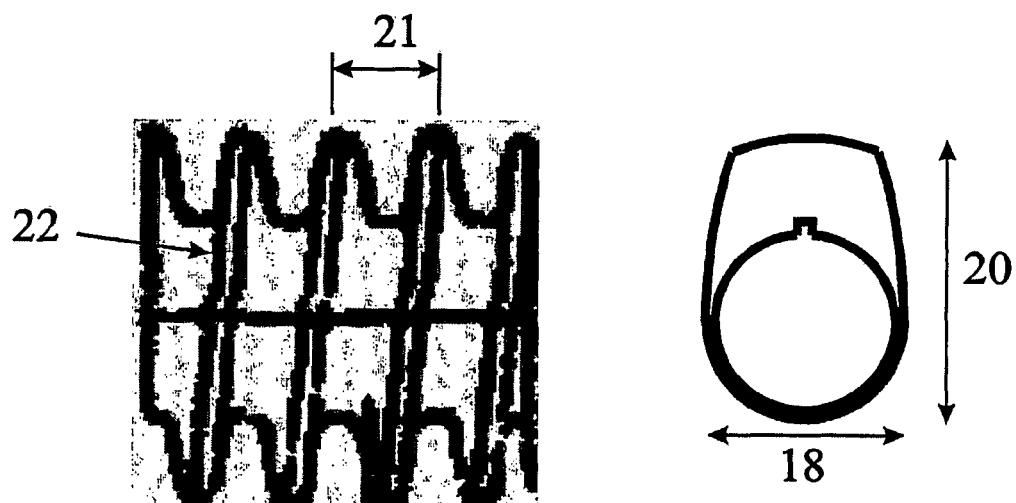
FIG. 6 illustrates an embodiment of a single lead screw element as used in the TSE. In this embodiment, the single lead screw pitch (21) was 12.7 mm; the flight width (22) was 2.7 mm; the inner (18) and outer (20) diameters were 27.7 and 38.3 mm respectively.
Figure 7:
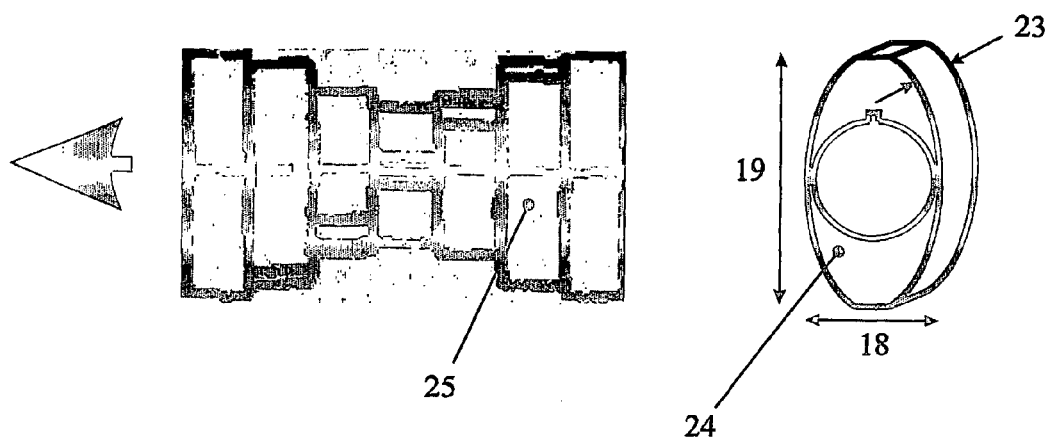
FIG. 7 illustrates an embodiment of a paddle block (25) as used in the TSE, and including seven single block elements having a forward staggering angle of 30°. In this embodiment, a single paddle block element (24) had a width (23) of 12.7 mm; the inner (18) and outer (19) diameters were 27.7 and 48.9 mm respectively.
Figure 8:
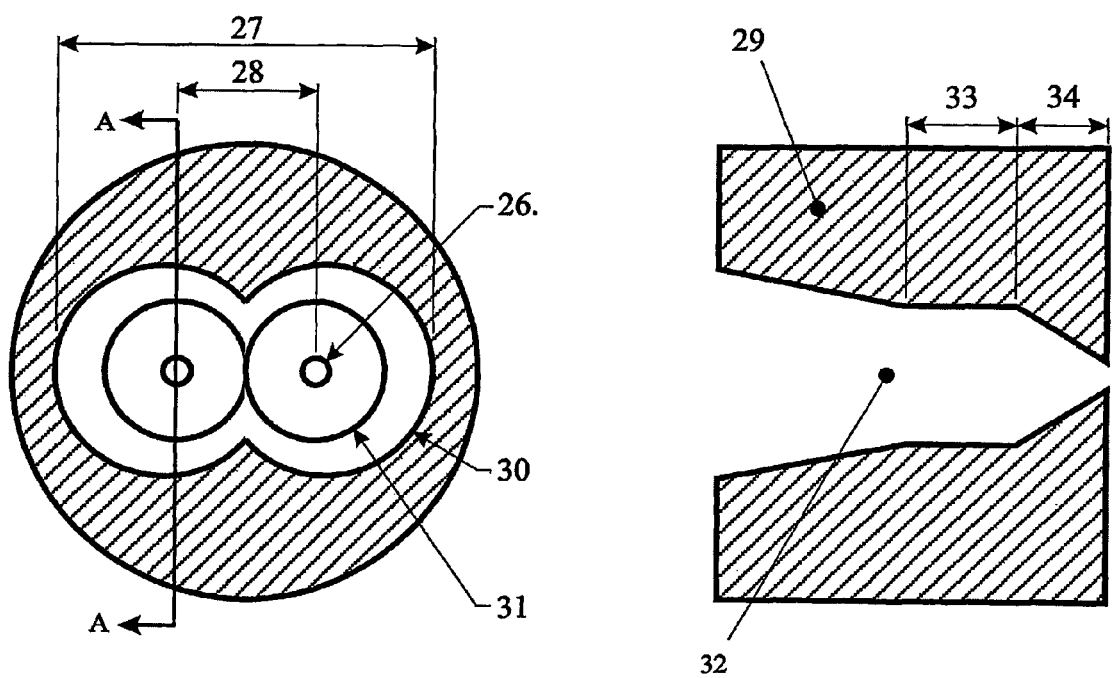
FIG. 8 illustrates an embodiment of the die geometry as well as the die cross-section (29) (along line A-A) as used in the TSE. In this embodiment, the die had two openings (26) of 6 mm respectively; the spacing (28) between the die openings was 30 mm; the uttermost spacing (27) between the screw barrels was 89 mm; the barrel diameter (30) was 50 mm; the length of the cylindrical portion of the die (33) was 38 mm and its diameter (30) 30 mm; the length of the conical transition (34) from the cylindrical portion to the die opening was 20 mm; and the total extrudate volume (32) of the die was 250 cm$^3$.

| Configuration | Manufacturer | Machine Code | $D_b$ | HP | Barrel & Screw design | Die design |
|---|---|---|---|---|---|---|
| SSE1 | Killion extruders | KLR 175 | 45 | 15 | FIGS. 1, 2 & Table 2 | FIG. 3 |
| SSE2 | | | | | FIGS. 1, 2 & Table 2 | FIG. 4 |
| TSE | Baker Perkins Food Machinery Division | MPF-50D | 50 | 25 | FIGS. 1, 5, 6, 7 & Table 2 | FIG. 8 |

TABLE 2

Screw design for both the SSE and TSE configuration.

Single Screw Design

| Configuration | h1 (mm) | h2 (mm) | l1 (mm) | l2 (mm) | b (mm) | $L_{tot}$ (mm) | e (mm) |
|---|---|---|---|---|---|---|---|
| SSE1 | 6.7 | 2.8 | 0 | 0 | 45 | 1080 | 4.5 |
| SSE2 | 11 | 5.1 | 216 | 540 | 34 | 1080 | 4.5 |

Twin Screw Design

Figure 5:
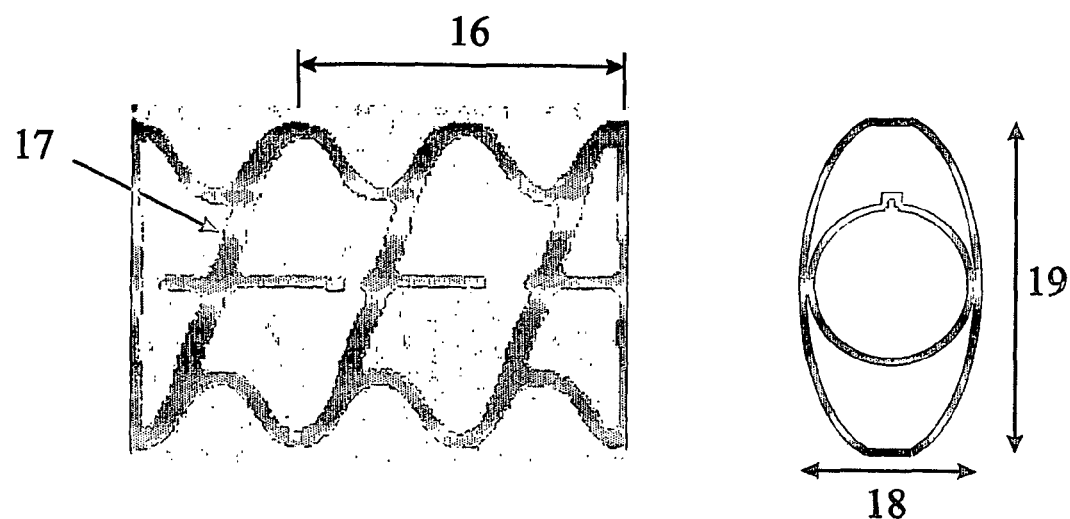
FIG. 5 illustrates an embodiment of a twin lead feed screw element as used in the TSE. In this embodiment, the twin lead feed screw pitch (16) was 50.8 mm; the flight width (17) was 1.5 mm; and the inner (18) and outer (19) diameters were 27.7 and 48.9 mm respectively.

| Feed port | Type of element | Description | Number of elements |
|---|---|---|---|
| | Twin lead feed screw | FIG. 5 | 4⅔ |
| | Single lead screw | FIG. 6 | 2 |
| | Paddle blocks | FIG. 7 | 21 (30° forward staggering angle) |
| Die | Single lead screw | FIG. 6 | 5½ |

Grinder

A Braun model KSM coffee grinder was used to grind the produced extrudate samples.

Test Methods

As discussed in Modern Superabsorbent Polymer Technology (Buchholz F. L. and Graham A. T. Eds., Wiley-VCH, New York, 1998, section 4.6.1. Swelling Capacity: Theory and Practice, p. 147), several methods of measurement are used in order to characterize the swelling capacity of a polymer. In the field of superabsorbents, the Gravimetric Swelling Capacity [also called the Free Swell Capacity (FSC)] and the Centrifuge Capacity [also called the Centrifuge Retention Capacity (CRC)] are recommended methods. The FSC and the CRC were used to compare the swelling capacities of the obtained absorbent products.

Tea Bags for FSC and CRC Measurements

Tea bags (6×6 cm) were made from heat sealable Ahlstrom™ filter paper (16.5±0.5 g/m²).

FSC Measurements

The Free Swell Capacity (FSC) in a 0.9% NaCl solution was determined according to the recommended test method 440.2-02 from EDANA (Free Swell Capacity No. 440.2-02, Recommended test Method: Superabsorbent materials-Polyacrylate superabsorbent powders-Free Swell Capacity in Saline by Gravimetric Determination, 2002).

CRC Measurements

The Centrifuge Retention Capacity (CRC) in a 0.9% NaCl solution was determined according to the recommended test method 441.2-02 from EDANA (Centrifuge Retention Capacity No. 441.2-02, Recommended Test Method: Superabsorbent materials-Polyacrylate superabsorbent powders-Determination of Fluid Retention Capacity in Saline Solution After Centrifugation, 2002).

Particle Size for FSC and CRC Measurements

All the FSC and CRC measurements were carried out using sieved products. Only particles ranging in size from 89 to 589 microns (−30 mesh/+170 mesh) were used for the FSC and CRC measurements.

Examples 1-16

Table 3 illustrates the effect on the FSC and CRC of different amylopectin/amylose blends extruded through a 8.5 mm diameter die. For each example, a paste was prepared by weighing 5 Kg of amylopectin/amylose blend (having a moisture content of about 9%), followed by adding 1.5 Kg of water to obtain a total moisture content of about 30%. The blends were prepared from common corn starch having an amylopectin content of 72%, and waxy maize starch having an amylopectin content of at least 99%. The pastes were hand-fed into SSE1 having the following barrel/die temperature profile: $Tb_1=50°$ C., $Tb_2=65°$ C., $Tb_3=135°$ C., $Td=135°$ C. The obtained extrudates were subsequently aged for 2 days at 85° C. in a convection oven and ground with a coffee grinder. As can be concluded from the results shown in Table 3, amylopectin extruded at low flow rates provides extrudates having superior FSC and CRC characteristics. Furthermore, starches having an amylopectin content of at least 90%, provide extrudates having significantly improved FSC and CRC characteristics.

TABLE 3

Effect on the FSC and CRC of different amylopectin/amylose blends extruded through a 8.5 mm diameter die.

Blend preparation before adding water

| # | % Waxy maize | % Common corn | % Amylopectin | Ω | Q | T | FSC | CRC |
|---|---|---|---|---|---|---|---|---|
| 1 | 0 | 100 | 72 | 25 | 9.6 | 140 | 8.6 | 5.1 |
| 2 | 0 | 100 | 72 | 40 | 8.6 | 138 | 8.1 | 5.3 |
| 3 | 0 | 100 | 72 | 55 | 23 | 139 | 8.2 | 5.1 |
| 4 | 50 | 50 | 86 | 24 | 4.1 | 141 | 10.4 | 8.3 |
| 5 | 50 | 50 | 86 | 40 | 9.5 | 140 | 10.5 | 8.6 |
| 6 | 50 | 50 | 86 | 55 | 11.3 | 137 | 9.8 | 8.0 |
| 7 | 66.7 | 33.3 | 90 | 15 | 4.4 | 142 | 13.4 | 10.3 |
| 8 | 66.7 | 33.3 | 90 | 31 | 7.4 | 141 | 13.9 | 10.8 |
| 9 | 66.7 | 33.3 | 90 | 43 | 9.8 | 141 | 15.0 | 8.6 |
| 10 | 66.7 | 33.3 | 90 | 55 | 12.8 | 140 | 14.6 | 7.9 |
| 11 | 85.2 | 14.8 | 95 | 15 | 4.4 | 141 | 17.5 | 12.4 |
| 12 | 85.2 | 14.8 | 95 | 31 | 9.6 | 140 | 16.6 | 13.2 |
| 13 | 85.2 | 14.8 | 95 | 43 | 11.5 | 138 | 17.5 | 11.1 |
| 14 | 100 | 0 | 99 | 10 | 4.5 | 141 | 19.5 | 15.0 |
| 15 | 100 | 0 | 99 | 25 | 7.6 | 140 | 20.7 | 14.5 |
| 16 | 100 | 0 | 99 | 37 | 12.3 | 141 | 21.6 | 12.2 |

Examples 17-18

Table 4 illustrates the effect of the die extrusion throughput ($Q_{die}$) and the die geometry on the FSC and CRC of the extrudates. The die extrusion throughput was controlled by a valve as illustrated in FIG. 4. A molecular network of self-entangled starch was formed with this die. For each example, a paste was prepared by weighing 5 Kg of a waxy maize starch (having a moisture content of about 9%), followed by adding 1.5 Kg of water to obtain a total moisture content of about 30%. The pastes were hand-fed into SSE2, turning 30 RPM, and having the following barrel/die temperature profile: $Tb_1=50°$ C., $Tb_2=65°$ C., $Tb_3=135°$ C., $Td=135°$ C. The obtained extrudates were subsequently aged for 2 days at 85° C. in a convection oven and ground with a coffee grinder. As can be concluded from the results shown in Table 4, a lower die extrusion throughput and using the die configuration as illustrated in FIG. 4, provides extrudates having superior FSC and CRC characteristics.

TABLE 4

Effect of the die extrusion throughput ($Q_{die}$) on the FSC and CRC of the extrudates.

| # | Q | $Q_{die}$ | T | FSC | CRC |
|---|---|---|---|---|---|
| 17 | 15.1 | 15.1 | 140 | 15.5 | 13.4 |
| 18 | 15.1 | 4.5 | 140 | 18.9 | 16.5 |

Examples 19-25

Table 5 illustrates the effect on the FSC and CRC of various amylopectin extrudates produced with or without crosslinking agent (also referred too as C-linker) using a TSE (die diameter of 6 mm). For each example, a paste was prepared by weighing 7 Kg of waxy maize starch (having a moisture content of about 9%), followed by adding 2.1 Kg of water to obtain a total moisture content of about 30%. The pastes were fed into the TSE (turning at 100 RPM) using a K-Tron T35™ volumetric feeder. When a cross-linking agent is used, the crosslinker is first dissolved in the water, along with the appropriate amount of sodium hydroxide, prior to adding the water to the waxy maize starch. The TSE had the following barrel/die temperature profile: $Tb_1=43°$ C., $Tb_2=59°$ C., $Tb_3=80°$ C., $Tb_4=108°$ C., $Tb_5=132°$ C., $Tb_6=151°$ C., $Tb_7=159°$ C., $Tb_8=159°$ C. (the die was not heated). The obtained extrudates were subsequently aged for 2 days at 60° C. in a convection oven and ground with a coffee grinder. As can be concluded from the results shown in Table 5, the FSC and CRC performances can be optimized using specific amounts of a given cross-linker and NaOH (Examples 20, 23 and 25).

TABLE 5

Effect on the FSC and CRC of various amylopectin extrudates produced with or without crosslinking agent.

| | | | (weight C-linker or NaOH/weight amylopectin) × 100% | | | |
|---|---|---|---|---|---|---|
| # | Q | C-linker* | C-linker | NaOH | T | FSC | CRC |
| 19 | 19.6 | None | 0 | 0 | 140 | 13.2 | 1.1 |
| 20 | 21.2 | MBA | 0.05 | 0.026 | 140 | 16.6 | 14.7 |
| 21 | 29.4 | None | 0 | 0 | 136 | 7.5 | 1.7 |
| 22 | 31.3 | STMP | 0.13 | 0.025 | 137 | 16.0 | 13.7 |
| 23 | 31.1 | STMP | 0.63 | 0.025 | 137 | 20.2 | 16.0 |
| 24 | 29.9 | STMP | 1.27 | 0.025 | 140 | 20.0 | 13.8 |
| 25 | 27.0 | ECH | 0.04 | 0.04 | 143 | 17.7 | 15.4 |

*ECH: Epichlorohydrin; STMP: Sodium Trimetaphosphate; MBA: N,N'-Methylenebisacrylamide Examples 26-27

Table 6 illustrates the effect of the aging process on the FSC and CRC of cross linked amylopectin extrudates. More specifically, crosslinked amylopectin extrudates aged at room temperature and in a convection oven at 60° C., are illustrated. A paste was prepared by weighing 7 Kg of waxy maize starch (having a moisture content of about 9%), followed by adding 2.1 Kg of an aqueous solution of sodium hydroxide (0.02% on a dry starch basis) comprising STMP (0.1% on a dry starch basis) to obtain a total moisture content of about 30%. The paste was fed into the TSE (turning at 100 RPM) at 33 Kg/h using a K-Tron T35™ volumetric feeder. The TSE had the following barrel/die temperature profile: $Tb_1=56°$ C., $Tb_2=79°$ C., $Tb_3=105°$ C., $Tb_4=144°$ C., $Tb_5=180°$ C., $Tb_6=196°$ C., $Tb_7=200°$ C., $Tb_8=204°$ C. (the die was not heated). The extrudate temperature was 144° C. As can be concluded from the results shown in Table 6, for an identical extrudate, a shorter aging process at higher temperatures provides extrudates having superior FSC and CRC characteristics.

TABLE 6

Effect of the aging process on the FSC and CRC of crosslinked amylopectin extrudates.

| # | Aging temperature | Aging time | FSC | CRC |
|---|---|---|---|---|
| 26 | Room temperature | 240 hours | 16.7 | 3.2 |
| 27 | 60° C. | 48 hours | 19.2 | 13.4 |

Examples 28-41

Table 7 illustrates the effect of the particle size of ground amylopectin extrudates on the FSC and CRC. The extrudates were obtained using a SSE having an 8.5 mm die diameter.

The extrudate (obtained from example 14) was ground with a coffee grinder and sieved using a Tyler Rota-Tap™ test sieve shaker.

TABLE 7

Effect of the particle size of ground amylopectin extrudates on the FSC and CRC.

| # | Particle size Mesh | Particle size Microns | FSC | CRC |
|---|---|---|---|---|
| 28 | +30 | >589 | 10.3 | 9.5 |
| 29 | −30/+40 | 417 to 589 | 15.9 | 14.4 |
| 30 | −40/+50 | 295 to 417 | 19.1 | 16.9 |
| 31 | −50/+60 | 246 to 295 | 21.3 | 18.7 |
| 32 | −60/+100 | 147 to 246 | 21.9 | 18.7 |
| 33 | −100/+170 | 89 to 147 | 17.4 | 14.4 |
| 34 | −170 | <89 | 20.7 | 10.5 |

Table 8 illustrates the effect of the particle size of ground STMP crosslinked amylopectin extrudates on the FSC and CRC. The extrudates were obtained using a TSE having an 6 mm die diameter. The extrudate (obtained from example 22) was ground with a coffee grinder and sieved using a Tyler Rota-Tap™ test sieve shaker.

TABLE 8

Effect of the particle size of ground STMP crosslinked amylopectin extrudates on the FSC and CRC.

| # | Particle size Mesh | Particle size Microns | FSC | CRC |
|---|---|---|---|---|
| 35 | +30 | >589 | 12.8 | 11.5 |
| 36 | −30/+40 | 417 to 589 | 15.7 | 14.0 |
| 37 | −40/+50 | 295 to 417 | 18.0 | 15.8 |
| 38 | −50/+60 | 246 to 295 | 18.9 | 16.2 |
| 39 | −60/+100 | 147 to 246 | 19.2 | 15.5 |
| 40 | −100/+170 | 89 to 147 | 18.4 | 14.0 |
| 41 | −170 | <89 | 14.7 | 7.4 |

As can be concluded from the results shown in Tables 7 and 8, good FSC and CRC characteristics are obtained with particles ranging in size from 89 to 589 microns.

Although the present invention has been described hereinabove by way of preferred embodiments thereof, it can be modified without departing from the spirit, scope and nature of the subject invention, as defined in the appended claims.

The invention claimed is:

1. An absorbent material comprising: particles formed from an extruded network of either cross-linked or self-entangled starch molecules, containing, at least 90% (w/w) of amylopectin; said starch molecules are gelatinized during an extrusion; and said particles range in size from 89 µm to 589 µm, and exhibit a free swell capacity (FSC) of at least 13 g/g and a centrifuge retention capacity (CRC) of at least 10 g/g in a 0.9% saline solution.

2. The absorbent material according to claim 1, wherein said starch network is produced from a waxy starch.

3. The absorbent material according to claim 2, wherein said waxy starch is selected from the group consisting of; waxy maize starch, waxy wheat starch, waxy rice starch, waxy sorghum starch, waxy potato starch, waxy cassava starch, waxy barley starch and mixtures thereof.

4. The absorbent material of claim 2, wherein said waxy starch is waxy maize starch.

5. A process for preparing the starch-based absorbent particle material of claim 1, the process comprising: providing starch molecules which contain at least 90% (w/w) of amylopectin, a starch-based paste with a cohesive plasticity and having a moisture content in a range from about 25% to about 45% (w/w); introducing said starch-based paste into an extruder; performing an extrusion with an extruder temperature of at least 130° C. to gelatinize said starch molecules and to develop a starch molecular network in an extrudate; aging said extrudate; and grinding said extrudate into particles.

6. The process according to claim 5, further comprises mixing said starch molecules with water, an alkali and a crosslinking agent.

7. The process according to claim 6, wherein said starch molecules are cross-linked during extrusion.

8. The process according to claim 5, wherein the paste includes from 0.001% to 02.0% (w/w on a dry starch basis) of said crosslinking agent.

9. The process according to claim 5, wherein the paste includes from 0.001% to 02.0% (w/w on a dry starch basis) of said alkali.

\* \* \* \* \*